(12) United States Patent
Cravo et al.

(10) Patent No.: US 8,329,698 B2
(45) Date of Patent: Dec. 11, 2012

(54) QUINOXALINEDIONE DERIVATIVES WHICH ARE ACTIVATORS OF AMPK-ACTIVATED PROTEIN KINASE

(75) Inventors: Daniel Cravo, Sartrouville (FR); Sophie Hallakou-Bozec, Montrouge (FR); Franck Lepifre, Longjumeau (FR)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 0 days.

(21) Appl. No.: 12/997,641

(22) PCT Filed: May 19, 2009

(86) PCT No.: PCT/EP2009/003538
§ 371 (c)(1),
(2), (4) Date: Dec. 13, 2010

(87) PCT Pub. No.: WO2009/152909
PCT Pub. Date: Dec. 23, 2009

(65) Prior Publication Data
US 2011/0130404 A1    Jun. 2, 2011

(30) Foreign Application Priority Data
Jun. 16, 2008  (EP) .................................. 08290564

(51) Int. Cl.
*A61K 31/495*  (2006.01)
*A61K 31/44*   (2006.01)

(52) U.S. Cl. ......... 514/249; 514/303; 544/350; 544/354

(58) Field of Classification Search .................. 514/249, 514/303; 544/350, 354
See application file for complete search history.

(56) References Cited

U.S. PATENT DOCUMENTS 5,631,373 A    5/1997  Cai et al.
5,977,107 A   11/1999  Cai et al.
2005/0176726 A1  8/2005  Wang et al.

FOREIGN PATENT DOCUMENTS
WO    02096422 A2    12/2002
WO   2005067932 A1    7/2005

OTHER PUBLICATIONS

World IP Organization. "International Search Report." PCT/EP2009/003538, Applicant: Merck Patent GMBH, Mailed: Jul. 23, 2009.
Horner, Leopold et al. "Derivatives of quinoxaline as isosteres of the pteridines." (Justus Liebig's Annalen Der Chemie), pp. 212-234, Jan. 1, 1953, vol. 579.
Ahmad Abid R et al. "Synthesis of some substituted quinoxalines and polycyclic systems containing the quinoxaline nucleus." (Journal of the Chemical Society), pp. 2443-2449, Jan. 1, 1996, vol. 1.
Cai S X et al. "Structure-Activity Relationships of Alkyl- and Alkoxy-Substituted 1,4-Dihydroquinoxaline-2,3-diones: Potent and Systemically Active Antagonists for the Glycine Site of the NMDA Receptor." (Journal of Medicinal Chemistry), pp. 730-738, Jan. 1, 1997, vol. 40, No. 5.

*Primary Examiner* — Douglas M Willis
(74) *Attorney, Agent, or Firm* — Millen, White, Zelano & Branigan, P.C.

(57) ABSTRACT

The present invention relates to compounds of formula (I)

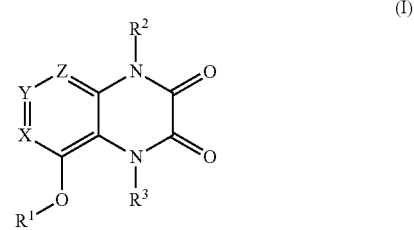

wherein X, Y, Z, $R^1$, $R^2$, $R^3$ are as defined in claim 1, including pharmaceutical compositions thereof and for their use in the treatment and/or prevention of diabetes, metabolic syndrome, obesity, cancer, inflammation.

2 Claims, No Drawings

QUINOXALINEDIONE DERIVATIVES WHICH ARE ACTIVATORS OF AMPK-ACTIVATED PROTEIN KINASE

FIELD OF THE INVENTION

The invention relates to quinoxalinedione derivatives that are activators of AMPK-activated protein kinase (AMPK) of formula (I).

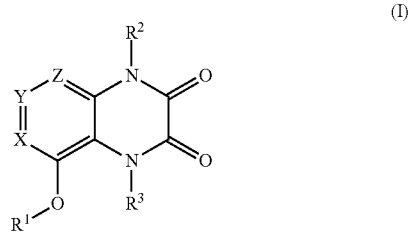

The invention also relates to the preparation and use of these quinoxalinedione in the treatment of disorders such as diabetes, metabolic syndrome, obesity, cancer, inflammation.

BACKGROUND OF THE INVENTION

The invention had the object of finding novel compounds having valuable properties, in particular those which can be used for the preparation of medicaments.

The present invention relates to compounds that are useful in the treatment and/or prevention of diseases such as diabetes, metabolic syndrome, obesity, cancer, inflammation.

Also provided are methods of treating diseases and disorders which can be treated by activating AMPK, comprising administering an effective amount of a compound of this invention.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

Surprisingly we have found that thienopyridone derivatives activate AMPK; therefore, these compounds are especially suitable for the prevention and treatment of diabetes, metabolic syndrome, obesity, cancer, inflammation. It has been found that the compounds according to the invention and salts thereof have very valuable pharmacological properties while being well tolerated. In particular, they exhibit AMPK activating effects.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

AMPK is well established as a sensor and regulator of cellular energy homeostasis (Hardie D. G. and Hawley S. A; "AMP-activated protein kinase: the energy charge hypothesis revisited" Bioassays, 23, 1112, (2001), Kemp B. E. et al. "AMP-activated protein kinase, super metabolic regulator", Biochem; Soc. Transactions, 31, 162 (2003)). Allosteric activation of this kinase due to rising AMP levels occurs in states of cellular energy depletion. The resulting serine/Threonine phosphorylation of target enzymes leads to an adaptation of cellular metabolism to low energy state. The net effect of AMPK activation induced changes is inhibition of ATP consuming processes and activation of ATP generating pathways, and therefore regeneration of ATP stores. Examples of AMPK substrates include acetyl-CoA carboxylase (ACC) and HMG-CoA-reductase (Carling D. at al., "A common bicyclic protein kinase cascade inactivates the regulatory enzymes of fatty acid and cholesterol biosynthesis", FEBS letters, 223, 217 (1987)). Phosphorylation and therefore inhibition of ACC leads to a decrease in fatty acid synthesis (ATP-consuming) and at the same time to an increase in fatty acid oxidation (ATP-generating). Phosphorylation and resulting inhibition of HMG-CoA-reductase leads to a decrease in cholesterol synthesis. Other substrates of AMPK include hormone sensitive lipase (Garton A. J. et al. "phosphorylation of bovine hormone-sensitive lipase by AMP-activated protein kinase; A possible antilipolytic mechanism", Eur. J. Biochem. 179, 249, (1989)), glycerol-3-phosphate acyltransferase (Muoio D. M. et al. "AMP-activated kinase reciprocally regulates triacylglycerol synthesis and fatty acid oxidation in liver and muscle: evidence that sn-glycerol-3-phosphate acyltransferase is a novel target", Biochem. J., 338, 783, (1999)), malonyl-CoA decarboxylase (Sarah A. K. et al., "activation of malonyl-CoA decarboxylase in rat skeletal muscle by contraction and the AMP-activated protein kinase activator-D-ribofuranoside", J. Biol. Chem., 275, □5-aminoimidazole-4-caboxamide-1-24279, (2000)).

AMPK is also implicated in the regulation of liver metabolism. Elevated glucose production by the liver is a major cause of fasting hyperglycemia in T2D (Saltiel et al., "new perspectives into the molecular pathogenesis and treatment of type 2 diabetes, cell 10, 517-529 (2001)). Gluconeogenesis in the liver is regulated by multiple enzymes such as phosphoenolpyruvate carboxykinase (PEPCK) and glucose-6-phosphatase-G6Pase). Activation of AMPK suppresses the transcription of theses genes in hepatoma cells (Lochhead et al, "5-aminoimidazole-4-carboxamide riboside mimics the effects of insulin on the expression of the 2 key gluconeogenic genes PEPCK and glucose-6-phosphatase, Diabetes, 49, 896-903 (2000)).

AMPK activation also down-regulates gluconeogenesis acting on some other genes expression. These effects may be due to its ability to down-regulate key transcription factors such as SREBP-1c (Zhou G. et al., "Role of AMP-activated protein kinase in mechanism of metformin action" J. Clin. Invest., 108, 1167 (2001)) ChREBP (Kawaguchi T. et al., "mechanism for fatty acids sparing effect on glucose induced transcription: regulation of carbohydrate response element binding protein by AMP-activated protein kinase" J. Biol. Chem. 277, 3829 involved in (Leclerc I. et al., "Hepatocyte nuclear factor-4□(2001)) or HNF-4 type 1 maturity-onset diabetes of the young is a novel target of AMP-activated protein kinase" Diabetes, 50, 1515 (2001)) or by direct phosphorylation of transcriptional coactivators such as p300 (Yang W; et al., "Regulation of transcription by AMP-activated protein kinase; Phosphorylation of p300 blocks its interaction with nuclear receptors" J. Biol. Chem 276, 38341 (2001)) and TORC2.

AMPK is considered as an attractive candidate for contraction-induced skeletal muscle glucose uptake because it is activated in parallel with elevation in AMP and a reduction in creatine phosphate energy stores (Hutber et al. "Electrical stimulation inactivates muscle acetyl—CoA carboxylase and increases AMP-activated protein kinase" Am. J. Physiol. Endocrinol. Metab. 272, E262-E66 (1997)). Furthermore, AICAR-induced activation of AMPK increases glucose uptake (Merrill et al. "AICA Riboside increases AMP-activated protein kinase, fatty acid oxidation and glucose uptake in rat muscle" Am. J. Physiol. Endocrinol. Metab. 273, E1107-E1112 (1997)) concomitantly with glucose transporter 4 (GLUT4) fusion with plasma membrane (Kurth-Kraczek "5'-AMP-activated protein kinase activation causes GLUT4 translocation in skeletal muscle, Diabetes, 48, 2☐ 1667-1671 (1999)). Over expression of an kinase dead subunit in skeletal muscle abolishes AICAR, but partially impairs contraction-stimulated glucose uptake (Mu J. et al. "A role for AMP-activated protein kinase in contraction and hypoxia-regulated glucose transport in skeletal muscle, Mol. Cell. 7, 1085-1094 (2001)). These findings suggest that additional pathways mediate contraction induced glucose uptake whereas it is apparent that AMPK mediates the effects of AICAR on glucose uptake.

Despite extensive study on upstream stimuli that activate AMPK, investigation on the downstream substrate(s) of AMPK-mediated glucose uptake is lacking. More recent reports revealed that Akt substrate of 160 kDa (AS160) is an important substrate downstream of Akt that is involved in insulin-stimulated glucose uptake. In addition to insulin, contraction and activation of AMPK by AICAR is associated with increased phosphorylation of AS160 in rodent skeletal muscle. Phosphorylation of AS160 is impaired or abolished in skeletal muscle from AMPK a2 knockout, g3 knockout, and a2-kinase dead mice in response to AICAR treatment (Treeback et al. AMPK-mediated AS160 phosphorylation in skeletal muscle is dependent on AMPK catalytic and regulatory subunits, Diabetes (2006)). This coroborates findings of impaired AICAR-stimulated glucose uptake in skeletal muscle of these mice (Jorgensen S. B. et al. Knockout of the a2 but not a 15'-AMP-activated protein kinase isoform abolishes 5-aminoimidazole-4-carboxamide-1b-4 ribofuranoside but not contraction-induced glucose uptake in skeletal muscle, J. Biol. Chem. 279, 1070-1079 (2004)). Therefore, AS160 appeared to be a downstream target of AMPK in mediating glucose uptake in skeletal muscle.

Taken together all these metabolic effects provide evidence that AMPK suppresses liver gluconeogenesis and lipid production, while decreasing hepatic lipid deposition via increased lipid oxidation, thus improving the glucose and lipid profile in T2D.

More recently an involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle (Minokoshi Y. et al, "leptin stimulates fatty-acid oxidation by activating AMP activated protein kinase", Nature, 415, 339 (2002)). Adiponectin another adipocyte derived hormone leading to improved carbohydrate and lipid metabolism, has been demonstrated to stimulated AMPK liver and skeletal muscle (Yamanauchi T. et al., "adiponectin stimulates glucose utilization and fatty acid oxidation by activating AMP-activated protein kinase", Nature Medicine, 8, 1288, (2002)), Tomas E. et al., "Enhanced muscle fat oxidation and glucose transport by ACRP30 globular domain: Acetyl-CoA carboxylase inhibition and AMP-activated protein kinase activation" PNAS, 99, 16309, (2002)). The activation of AMPK in these circumstances seems to be independent of increasing cellular AMP levels but rather due to phosphorylation by one or more yet to be identified upstream kinases.

Based on the knowledge of the above-mentioned consequences of AMPK activation, profound beneficial effects would be expected from in vivo activation of AMPK. In liver, decreased expression gluconeogenic enzymes would reduce hepatic glucose output and improve overall glucose homeostasis, and both direct inhibition and/or reduced expression of key enzymes in lipid metabolism would increase glucose uptake and fatty acid oxidation with resulting improvement of glucose homeostasis and, due to a reduction in intra-myocyte triglyceride accumulation, to improved insulin action. Finally, the increase in energy expenditure should lead to a decrease in body weight. The combination of these effects in the metabolic syndrome would be expected to significantly reduce the risk for acquiring cardiovascular diseases.

Several studies in rodents support this hypothesis (Bergeron R. et al. "Effect of 5-aminoimidazole-4-carboxamide-1 (beta)-D-rifuranoside infusion on in vivo glucose metabolism in lean and obese Zucker rats", Diabetes, 50, 1076 (2001), Song S. M. et al., 5-aminoimidazole-4-dicarboxamide ribonucleoside treatment improves glucose homeostasis in insulin-resistant diabeted (ob/ob) mice", Diabetologia, 45, 56 (2002), Halseth A. E. et al., "Acute and chronic treatment of ob/ob and db/db mice with AICAR decreases blood glucose concentrations", Biochem. and Biophys. Res. Comm., 294, 798 (2002), Buhl E. S. et al., "Long-term AICAR administration reduces metabolic disturbances and lowers blood pressure in rats displaying feature of the insulin resistance syndrome", Diabetes, 51, 2199 (2002)). Until recently most in vivo studies have relied on the AMPK activator AICAR, a cell permeable precursor of ZMP. ZMP acts as an intracellular AMP mimic and, when accumulated to high enough levels, is able to stimulate AMPK activity (Corton J. M. et al. "5-aminoimidazole-4-dicarboxamide ribonucleoside, a specific method for activating AMP-activated protein kinase in intact cells?", Eur. J. Biochem., 229, 558 (1995)). However, ZMP also acts as an AMP mimic in the regulation of other enzymes, and therefore not a specific AMPK activator (Musi N. and Goodyear L. J., "Targeting the AMP-activated protein kinase for the treatment of type 2 diabetes", Current Drug Targets-immune, Endocrine and Metabolic Disorders, 2 119 (2002)). Several in vivo studies have demonstrated beneficial effects of both acute and chronic AICAR administration in rodent models of obesity and type 2 diabetes (Bergeron R. et al., "Effect of 5-aminoimidazole-4-carboximide-1b-D ribofuranoside infusion on in vivo glucose metabolism in lean and obese Zucker rats", Diabetes, 50, 1076, (2001), Song S. M. et al., "5-aminoimidazole-4-carboxamide ribonucleotide treatment improves glucose homeostasis in insulin resistant diabetic (ob/bo) mice", Diabetologia, 45, 56, (2002), Halseth A. E. et al., "Acute and chronic treatment of ob/ob and db/db mice with AICAR decreases blood glucose concentrations" Biochem. Biophys. Res. Comm. 294, 798, (2002), Buhl E. S. et al., "Long-term AICAR administration reduces metabolic disturbances and lowers blood pressure in rats displaying feature of the insulin resistance syndrome", Diabetes, 51, 2199 (2002)). For example, 7 week AICAR administration in the obese Zucker (fa/fa) rat leads to a reduction in plasma triglycerides and free fatty acids, an increase in HDL cholesterol, and a normalisation of glucose metabolism as assessed by an oral glucose tolerance test (Minokoshi Y. et al., "Leptin stimulates fatty-acid oxidation by activating AMP-activated protein kinase", Nature, 415, 339,-2002)). In both ob/ob and db/db mice, 8 day AICAR administration reduces blood glucose by 35% (Halseth A. E. et al., "Acute and chronic treatment of ob/ob and db/db mice with AICAR decreases blood glucose concentrations", Biochem. Biophys. Res. Comm., 294, 798 (2002)). In addition to AICAR, it was found that the diabetes drug metformin can activate AMPK in vivo at high concentrations (Zhou G. et al., "Role of AMP-activated protein kinase in mechanism of metformin action", J. Clin. Invest, 108, 1167, (2001), Musi N. et al., "Metformin increases AMP-activated protein kinase activity in skeletal muscle of subjects with type 2 diabetes", Diabetes, 51, 2074, (2002)), although it has to be determined to what extent its antidiabetic action relies on this activation. As with leptin and adiponectin, the stimulatory effect of metformin is indirect via activation of an upstream kinase (Zhou G. et al., "Role of AMP-activated protein kinase in mechanism of metformin action", J. Clin. Invest., 108, 1167, (2001)). More recently, a small molecule AMPK activator have been described. This direct AMPK activator, named A-769662, a member of the Thienopyridone family in vivo induces a decrease in plasma glucose and triglycerides (Cool. B. et al., "Identification and characterization of a small molecule AMPK activator that treats key components of type 2 diabetes and the metabolic syndrome", cell Metab., 3, 403-416, (2006)).

In addition to pharmacologic intervention, several transgenic mouse models have been developed in the last years, and initial results are becoming available. Expression of dominant negative AMPK in skeletal muscle of transgenic mice has demonstrated the AICAR effect on stimulation of glucose transport is dependant of AMPK activation (Mu J. et al., "Role for AMP-activated protein kinase in contraction and hypoxia regulated glucose transport in skeletal muscle", Molecular Cell, 7, 1085, (2001)), and therefore likely not caused by non-specific ZMP effects. Similar studies in other tissues will help to further define the consequences of AMPK activation. It is expected that pharmacologic activation of AMPK will have benefits in the metabolic syndrome with improved glucose and lipid metabolism and a reduction in body weight. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference, and blood lipid changes as defined by increase in triglycerides above 150 mg/dl or decrease HDL cholesterol below 40 mg/dl (men) or 50 mg/dl (women). Therefore, the combined effects that may be achieved through activation of AMPK in a patient who qualifies as having metabolic syndrome would raise the interest of this target.

Stimulation of AMPK has been shown stimulate expression of uncoupling protein 3 (UCP3) skeletal muscle (Zhou m. et al., "UCP-3 expression in skeletal muscle: effects of exercise, hypoxia, and AMP-activated protein kinase", AM. J. Physiol. Endocrinol. Metab., 279, E622, (2000)) and might therefore be a way to prevent damage from reactive oxygen species. Endothelial NO synthase (eNOS) has been shown to be activated through AMPK mediated phosphorylation (Chen Z.-P. et al., "AMP-activated protein kinase phosphorylation of endothelial NO synthase", FEBS Letters, 443, 285, (1999)), therefore AMPK activation can be used to improve local circulatory systems.

AMPK has a role in regulating the mTOR pathway. mTOR is a serine/threonine kinase and is a key regulator of protein synthesis. To inhibit cell growth and protect cells from apoptosis induced by glucose starvation, AMPK phosphorylates TSC2 at Thr-1227 and Ser-1345 increasing the activity of the TSC1 and TSC-2 complex to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signalling pathway. Treatment of various cancer cell lines by AICAR attenuated the cell proliferation both in vitro and in vivo studies (Giri R; R., "5-Aminoimidazole-4-carboxamide-1-beta-4-ribofuranoside inhibits cancer cell proliferation in vitro and in vivo via AMP-activated protein kinase (AMPK)", J. Biol. Chem. (2005)). Two reports link the treatment of metformin with a lower risk of cancer in diabetic patients (Evans J. M. "Metformin and reduced risk of cancer in diabetic patients", BMJ, 330, 1304-1305, (2005))

The activation of AMPK by AICAR has been shown to reduce expression of the lipogenic enzymes FAS and ACC, resulting in suppression of proliferation in prostatecancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

In some publications it has been described that AICAR as an AMPK activator exerts anti-inflammatory diseases. It has been observed that AICAR attenuates the production of proinflammatory cytokines and mediators (S. Giri et al. J. Neuroscience 2004, 24:479-487), AICAR in rat model and in vitro attenuates EAE progression by limiting infiltration of leucocytes across blood brain barrier (BBB) (N. Nath. Et al. J. of Immunology 2005, 175:566-574; R. Prasad et al. J. Neurosci Res. 2006, 84:614-625) and it has been suggested recently that AMPK activating agents act as anti-inflammatory agents and can hold a therapeutic potential in Krabbe disease/twitcher disease (an inherited neurological disorder) (S. Giri et al. J. Neurochem. 2008, Mar. 19).

PRIOR ART

WO 9512417 discloses 1,4-dihydroquinoxaline-2,3-dione for treating or preventing neuronal loss associated with stroke, ischemia, CNS trauma, hypoglycemia, and surgery, as well as treating neurodegenerative diseases including Alzheimer's disease, amyotrophic lateral sclerosis, Huntington's disease, and Down's syndrome, treating or preventing the adverse consequences of the hyperactivity of the excitatory amino acids, as well as treating anxiety, chronic pain, convulsions, and inducing anesthesia are disclosed by administering to an animal in need of such treatment an alkyl or azido-substituted 1,4-dihydroquinoxaline-2,3-dione or pharmaceutically acceptable salts thereof, which have high binding to the glycine receptor.

WO 9835948 discloses N-substituted 5-aminoethoxy-1,4-dihydroquinoxaline-2,3-dione derivatives which are dopamine D2 agonists used as antipsychotic agents and antiparkinson agents.

US2005/0176726 discloses 1,4-dihydroquinoxaline-2,3-dione as an intermediate of synthesis in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

SUMMARY OF THE INVENTION

The invention relates to 1,4-dihydroquinoxaline-2,3-diones of the formula (I)

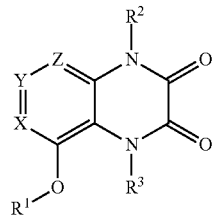

in which
X, Y, Z each, independently of one another, denote N or $CR^4$, excluding compounds wherein X=Z=N,
$R^1$ denotes H, A, COA, $COOR^5$, $CONR^6R^7$, Ar or Het,
$R^2$, $R^3$ each, independently of one another, denote H or A',
$R^4$ denotes H, A, OH, OA, Hal, $NH_2$, NHA, $NA_2$, $NO_2$, COA, $COOR^5$, $CONR^6R^7$, CN, Ar or Het,
$R^5$ denotes H or A',
$R^6$, $R^7$ each, independently of one another, denote H, A, Ar or $Het^1$, $R^6$ and $R^7$ together also denote $(CH_2)_m$,
Ar denotes phenyl, naphthyl or biphenyl, each of which is unsubstituted or mono-, di-, tri-, tetra- or pentasubstituted by A, Hal, OA, OH, CHO, COA, $NH_2$, NHA, $NA_2$, $NO_2$, COOA, COOH, $CONH_2$, CONA, $CONA_2$, $SO_2A$, CN, C(=NH)$NH_2$ and/or C(=NH)NHOH,
Het denotes a mono- or bicyclic saturated, unsaturated or aromatic heterocycle having 1 to 4 N, O and/or S atoms, which may be mono-, di- or trisubstituted by Hal, A, OA, OH, CHO, COA, COOH, COOA, CN, $NO_2$, $NH_2$, NHA, $NA_2$, $CONH_2$, CONHA, $CONA_2$ and/or =O,
$Het^1$ denotes a mono- or bicyclic unsaturated or aromatic heterocycle having 1 to 4 N, O and/or S atoms, which may be mono-, di- or trisubstituted by Hal, A, OA, OH, CHO, COA, COOH, COOA, CN, $NO_2$, $NH_2$, NHA, $NA_2$, $CONH_2$, CONHA and/or $CONA_2$,
A denotes unbranched or branched alkyl having 1-10 C atoms, in which one or two non-adjacent CH and/or $CH_2$ groups may be replaced by O and/or NH and/or in addition 1-7 H atoms may be replaced by OH, F and/or Cl,
or denotes cycloalkyl having 3-7 C atoms,
A' denotes unbranched or branched alkyl having 1-6 C atoms, in which 1-7 H atoms may be replaced by F and/or Cl,
Hal denotes F, Cl, Br or I,
m 2, 3, 4, 5 or 6,
and pharmaceutically usable salts and stereoisomers thereof, including mixtures thereof in all ratios.
Some preferred compounds of formula (I) are selected from the group
5-hydroxy-1,4-dihydroquinoxaline-2,3-dione,
acetic acid 2,3-dioxo-1,2,3,4-tetrahydro-quinoxalin-5-yl ester,
5-methoxy-1,4-dihydroquinoxaline-2,3-dione,
5-hydroxy-4-methyl-1,4-dihydroquinoxaline-2,3-dione,
5-hydroxy-1,4-dimethyl-1,4-dihydroquinoxaline-2,3-dione,
1,4-dimethyl-5-methoxy-1,4-dihydroquinoxaline-2,3-dione,
2,2-dimethyl-propionic acid 2,3-dioxo-1,2,3,4-tetrahydro-quinoxalin-5-yl ester,
8-methoxy-1-methyl-1,4-dihydro-quinoxaline-2,3-dione,
4,6-dihydro-1H-pyrido[3,4-b]pyrazine-2,3,5-trione,
8-hydroxy-1,4-dihydro-pyrido[2,3-b]pyrazine-2,3-dione,
5-methoxy-1-methyl-1,4-dihydroquinoxaline-2,3-dione,
5-hydroxy-1-methyl-1,4-dihydroquinoxaline-2,3-dione,
5-(2-hydroxy-ethoxy)-1,4-dihydro-quinoxaline-2,3-dione,
and pharmaceutically usable salts and stereoisomers thereof, including mixtures thereof in all ratios.
The invention relates to the compounds of the formula (I) and salts thereof and to a process for the preparation of compounds of the formula (I) according to claims 1-7 and pharmaceutically usable salts and stereoisomers thereof, characterised in that a compound of the formula (II)

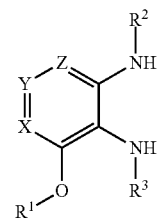

in which
$R^1$, $R^2$, $R^3$, X, Y and Z have the meanings indicated in claim 1,
is reacted with a compound of the formula (III)

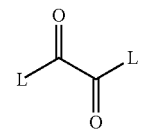

in which
L denotes Cl, Br, I or a free or reactively functionally modified OH group,
and/or
a base or acid of the formula I is converted into one of its salts.
Compounds of the formula (II) are commercially available (chemos Gmbh, Fluorochem, Acros, Interchim) or synthesized by methods known to the skilled man, e.g. preparation of anthranylic derivatives [Advanced Organic Chemistry; A. Carey and J. Sunberg, 4$^{th}$ edition, page 722; nucleophilic addition by an amine derivative such as ammoniac, small alkylamine on an aromatic cycle such as benzene activated by an electroattractive group such as nitro group, a carboxylic group].
L in formula (III) preferably denotes Cl, imidazolyl, $OCH_3$ or $OC_2H_5$. Compounds of the formula (III) are commercially available (Acros, Interchim). The diamino derivatives of the formula (II) add by a nucleophilic addition to an oxalyl compound (III) in an inert solvent preferably in an aprotic solvent more preferably in tetrahydrofurane, dioxane, toluene at 20° C. to 150° C. preferably 60 to 120° C. for 30 minutes to 24 hours preferably from 30 minutes to 1 hour.
Suitable inert solvents are, for example, hydrocarbons, such as hexane, petroleum ether, benzene, toluene or xylene;

chlorinated hydrocarbons, such as trichloroethylene, 1,2-dichloroethane, carbon tetrachloride, chloroform or dichloromethane; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The invention also relates to the racemic forms, tautomeric forms, enantiomers, diastereoisomers epimers and, organic or mineral salts of the compounds of the general formula (I), as well as their crystalline forms, including their polymorphic forms and the polymorphic forms of the compounds of formula (I).

Compounds of formula (I) also mean their pharmaceutically usable derivatives and their solvates.

The present invention is directed not only to racemic mixtures of these compounds, but also to individual stereoisomers and/or diastereoisomers thereof as well or as mixtures of these in all proportions.

The invention also relates to the stereoisomers (including E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Compounds of formula I also mean their tautomers such as the two following species

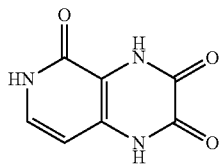 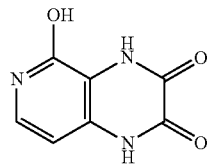

Pharmaceutically usable derivatives is taken to mean, for example, the salts of the compounds according to the invention and also so-called prodrug compounds.

Prodrug derivatives is taken to mean compounds of the formula I which have been modified, with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence:

improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, their meanings are independent of one another.

Above and below, the radicals and parameters $R^1$, $R^2$, $R^3$, X, Y and Z have the meanings indicated for the formula (I), unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, iso-propyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-tri-methylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A preferably denotes unbranched or branched alkyl having 1-10 C atoms, in which 1-7 H atoms may be replaced by OH, F and/or Cl.

Cycloalkyl denotes a monovalent carbocyclic radical of 3 to 10 carbon atoms, preferably 3 to 6 carbon atom such as cyclopropyl, cyclobutyl, cyclopentyl or cyclohexyl.

Moreover A denotes alkyl in which one or two non-adjacent CH and/or $CH_2$ groups may be replaced by O and/or NH, preferably $CH_2OCH_3$, $CH_2CH_2OCH_3$, $CH_2CH_2NH_2CH_2CH_3$.

A' denotes alkyl, is unbranched (linear) or branched, and has 1, 2, 3, 4, 5, 6 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-tri-methylpropyl, further preferably, for example, trifluoromethyl.

A' very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

X preferably denotes N or $CR^4$.
Y preferably denotes $CR^4$.
Z preferably denotes N or $CR^4$.
$R^1$ preferably H, A or COA.
$R^2$ preferably denotes H or methyl.
$R^3$ preferably denotes H or methyl.
$R^4$ preferably denotes H.
$R^6$, $R^7$ preferably denote H oder A, most preferably H.
Ar denotes, for example, phenyl, o-, m- or p-tolyl, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-ureidophenyl, o-, m- or p-formylphenyl, o-, m- or p-acetylphenyl, o-, m- or p-aminosulfonyl-phenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxy-phenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably. 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-; 5-, 6-; 7- or 8-innolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals can also be partially or fully hydrogenated.

Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a mono- or bicyclic aromatic heterocycle having 1 to 4 N, O and/or S atoms, Most preferably Het denotes pyridyl, pyrimidinyl, furanyl, isoxazolyl; imidazolyl, pyrazolyl, oxazolyl, pyrrolyl, thiazolyl, isothiazolyl, thienyl, triazolyl, tetrazolyl, indolyl, benzimidazolyl or indazolyl.

$Het^1$ preferably denotes pyridyl, pyrimidinyl, furanyl, isoxazolyl, imidazolyl, pyrazolyl, oxazolyl, pyrrolyl, thiazolyl, isothiazolyl, thienyl, triazolyl, tetrazolyl, indolyl, benzimidazolyl or indazolyl.

Accordingly, the invention relates, in particular, to the compounds of the formula (I) in which at least one of the said radicals has one of the preferred meanings indicated above. Some preferred groups of compounds may be expressed by the following sub-formulae Ia to Ie, which conform to the formula (I) and in which the radicals not designated in greater detail have the meaning indicated for the formula I, but in which
in Ia X denotes N or $CR^4$,
  Y denotes $CR^4$,
  Z denotes N or $CR^4$;
in Ib denotes H, A or COA;
in Ic $R^4$ denotes H;
in Id A denotes unbranched or branched alkyl having 1-10 C atoms;
  in which 1-7 H atoms may be replaced by OH, F and/or Cl;
in Ie X denotes N or CH,
  Y denotes CH,
  Z denotes N or CH,
    excluding compounds wherein X=Z=N,
  $R^1$ denotes H, A or COA,
  $R^2$, $R^3$ each, independently of one another, denote H or A',
  A denotes unbranched or branched alkyl having 1-10 C atoms,
    in which 1-7 H atoms may be replaced by OH, F and/or Cl, or
    denotes cycloalkyl having 3-7 C atoms,
  A' denotes unbranched or branched alkyl having 1-6 C atoms,
    in which 1-7 H atoms may be replaced by F and/or Cl;
and pharmaceutically usable salts and stereoisomers thereof, including mixtures thereof in all ratios.

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, potassium tertiobutylate, sodium tertioamylate, triethylamine, potassium hexamethyldisilazide, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether, dioxane and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

Pharmaceutical Salts and Other Forms

The said compounds according to the invention can be used in, their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitro benzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula (I) which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethyl-amine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula (I) according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereoisomers are formed from the mixture by reaction with an optically active resolving agent. Examples of suitable resolving agents are optically active acids, such as the R and S forms of tartaric acid; diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

For chiral resolution of the racemates following acids and amines can be used: As examples, the following chiral acids can be used: (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphoric acid, (−)-camphoric add, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethyl-cellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acacia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions; pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants; buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

EXAMPLES

The following examples illustrate the invention without, however, limiting it. The starting materials used are known products or products prepared according to known procedures. The percentages are expressed on a weight basis, unless otherwise mentioned.

The compounds are characterised especially via the following analytical techniques.

The NMR spectra are acquired using a Bruker Avance DPX 300 MHz NMR spectrometer.

The masses are determined by HPLC coupled to an Agilent Series 1100 mass detector. The melting points (m.p.) were measured on a Stuart Scientific block.

Example 1

5-hydroxy-1,4-dihydroquinoxaline-2,3-dione

A solution of 2,3-diaminophenol (50 g). and 1,1'-oxalyldiimidazole (92 g) and tetrahydrofurane (1.2 L) is refluxed 30 minutes. The solvent is removed under reduced pressure and the remaining solid taken into ethyl acetate. The organic phase is washed with 1M aqueous hydrochloric solution, dried over sodium sulphate and concentrated under vacuum. The crude solid obtained is recrystallised from dimethylformamide; yield: 14.8 g; MS: 177.1 (M−1);

$^1$H NMR (DMSO-d$_6$, 300 MHz): δ [ppm] 6.61 (m, 2H); 6.91 (ss, 1H), 10.21 (s(1H); 11.05 (s, 1H); 11.85 (s, 1H).

Example 2

8-Hydroxy-1,4-dihydro-pyrido[2,3-b]pyrazine-2,3-dione

Step 1: A solution of 2-chloro-4-hydroxy-3-nitro-pyridine (1.95 g) in concentrated aqueous ammonia solution (100 mL) is stirred 3 days at 110° C. in a sealed vessel. The reaction mixture is partially concentrated; then the precipitate formed is collected, washed with water and ethyl acetate; yield: 1.1 g of a brown solid was obtained; MS: 154.1 (M−1);

$^1$H NMR (DMSO-d$_6$, 300 MHz): δ [ppm] 5.78 (d, 1H); 7.27 (d, 1H); 7.69 (s, 2H); 10.62 (bs, 1H)

Step 2: The previous compound (1.1 g), 10% palladium on carbon (200 mg) in a mixture of methanol/dimethylformamide (20 mL/20 mL) is stirred under a hydrogen atmosphere during 1 day. The solution is filtered and the solvents removed under reduced pressure. The crude solid is recrystallised from methanol. 559 mg of a brown solid is obtained; MS: 124.1 (M−1);

$^1$H NMR (DMSO-d$_6$, 300 MHz): δ [ppm] 6.15 (d, 1H); 7.15 (d, 1H)

Step 3: The previous compound (559 mg) and oxalic acid dihydrate (1.15 g) in a solution of 4M aqueous hydrochloric acid (50 mL) are heated at reflux overnight. The precipitate formed under cooling is recovered, washed with water and ethyl acetate. 250 mg of a dark green solid were obtained; MS: 178.1 (M−1);

$^1$H NMR (DMSO-d$_6$, 300 MHz): δ [ppm] 6.68 (d, 1H) 7.82 (d, 1H); 11:40 (bs, 1H);

$^{13}$C NMR (DMSO-d$_6$, 75.5 MHz): δ [ppm] 107.36 and 141.18 (CH); 111.23, 139.02, 153.32, 154.72, 156.34 (C quaternar).

Example 3

5-methoxy-1-methyl-1,4-dihydroquinoxaline-2,3-dione

Step 1: A solution of 1-fluoro-3-methoxy-2-nitro-phenyl (2.36 g) and 40% aqueous methylamine (16.1 mL) in methanol (50 mL) is heated at 70° C. overnight. The solvent is removed under reduced pressure and the crude taken up into ethyl acetate. The organic solution is washed with water then dried over sodium sulphate. A red solid (2.33 g) crystallises after removal of the solvent;

$^1$H NMR (DMSO-d$_6$, 300 MHz): δ [ppm] 2.72 (d, 3H); 3.78 (s, 3H); 6.17 (q, 1H); 6.37 (d, 1H); 6.40 (d, 1H); 7.27 (dd, 1H).

Step 2: The previous solid (3.13 g) and 10% palladium on carbon (500 mg) in methanol (50 mL) are stirred under hydrogen atmosphere overnight. The solution is filtered over celite and the solvent removed under reduced pressure. 2.5 g of a black solid are obtained;

$^1$H NMR (DMSO-d$_6$, 300 MHz): δ [ppm] 2.70 (d, 3H); 3.71 (s, 3H); 3.98 (bs, 2H); 4.61 (q, 1H); 6.15 (d, 1H); 6.28 (d, 1H); 6.52 (dd, 1H).

Step 3: The previous compound (2.48 g) and oxalic acid dihydrate (4.2 g) in a solution of 4M aqueous hydrochloric acid (100 mL) are heated at reflux overnight. The precipitate formed under cooling is recovered, washed with water and ethyl acetate. 2.12 g of a grey solid are obtained; MS: 207.1 (M+1);

$^1$H NMR (DMSO-d$_6$, 300 MHz): δ [ppm] 3.49 (s, 3H); 3.85 (s, 3H); 6.88 (d, 1H); 6.95 (d, 1H); 7.13 (dd, 1H); 11.26 (bs, 1H), Biological Assays Enzymatic Activity The following biological test allows the determination of the efficacy of such compounds of formula (I) onto AMPK protein (recombinant α1β1γ2).

Human recombinant AMPK enzyme was expressed in *E. Coil* and was reactivated in vitro by LKB1 prior to enzyme activity determination. AMPK enzyme activities were assayed by using A Delfia technology. AMPK enzyme activities were carried out in microtiter plates (50 mM Hepes buffer, pH 7.4 with 125 μM ATP respectively) in the presence of a synthetic peptide substrate (AMARAASAAALARRR, the "AMARA" peptide) and activators in serial dilutions. Reactions were initiated by the addition of AMPK (50-100 ng). Following mixing, the plates were incubated for 30 min at room temperature. Enzyme activity was assayed by using an anti-phosphoserine antibody to measure the quantity of phosphate incorporated into the AMARAA.

Activity:

Ratio between the % of control (basal activity) of compound of formula (I) at 30 μM and the % of control (basal activity) of AMP (natural substrate) at 30 μM.

Compounds of formula (I) are considered as direct activator of AMPK if the ratio is 90% or higher.

These following compounds illustrated the biological "in vitro" activity 5-hydroxy-1,4-dihydroquinoxaline-2,3-dione: 130%

Acetic acid 2,3-dioxo-1,2,3,4-tetrahydro-quinoxalin-5-yl ester: 120%

The following examples relate to pharmaceutical preparations:

Example A

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient according to the invention, 9.38 g of NaH$_2$PO$_4$.2H$_2$O, 28.48 g of Na$_2$HPO$_4$.12H$_2$O and 0.1 g benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient according to the invention are mixed with 99.5 g of Vaseline under aseptic conditions.

Example E

Tablets

A mixture of 1 kg of active ingredient according to the invention, 4 kg of lactose, 1.2 kg of potato. starch, 0.2 kg of talc and 0.1 kg of magnesium stearate is pressed to give tablets in a conventional manner in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient according to the invention are introduced into hard gelatine capsules in a conventional manner in such a way that each capsule contains 20 mg of the active ingredient.

Example H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. A compound selected from the group consisting of:
acetic acid 2,3-dioxo-1,2,3,4-tetrahydro-quinoxalin-5-yl ester,
5-hydroxy-4-methyl-1,4-dihydroquinoxaline-2,3-dione,
5-hydroxy-1,4-dimethyl-1,4-dihydroquinoxaline-2,3-dione,
1,4-dimethyl-5-methoxy-1,4-dihydroquinoxaline-2,3-dione,
2,2-dimethyl-propionic acid 2,3-dioxo-1,2,3,4-tetrahydro-quinoxalin-5-yl ester,
8-methoxy-1-methyl-1,4-dihydro-quinoxaline-2,3-dione,
4,6-dihydro-1H-pyrido[3,4-b]pyrazine-2,3,5-trione,
8-hydroxy-1,4-dihydro-pyrido[2,3-b]pyrazine-2,3-dione,
5-methoxy-1-methyl-1,4-dihydroquinoxaline-2,3-dione,
5-hydroxy-1-methyl-1,4-dihydroquinoxaline-2,3-dione,
5-(2-hydroxy-ethoxy)-1,4-dihydro-quinoxaline-2,3-dione,
and pharmaceutically usable salts and stereoisomers thereof, including mixtures thereof in all ratios.

2. A composition comprising at least one compound according to claim 1, or a pharmaceutically usable salt or stereoisomer thereof, including mixtures thereof in all ratios, and a pharmaceutically acceptable excipient or adjuvant.

* * * * *